US011801361B2

(12) United States Patent
Stark et al.

(10) Patent No.: US 11,801,361 B2
(45) Date of Patent: Oct. 31, 2023

(54) ANESTHETIC DISPENSING DEVICE WITH A MEASURING UNIT

(71) Applicant: Drägerwerk AG & Co. KGaA, Lübeck (DE)

(72) Inventors: Hartmut Stark, Lübeck (DE); Norbert Wruck, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 342 days.

(21) Appl. No.: 17/149,109

(22) Filed: Jan. 14, 2021

(65) Prior Publication Data

US 2021/0220602 A1   Jul. 22, 2021

(51) Int. Cl.
*A61M 16/18* (2006.01)
*A61M 16/00* (2006.01)
*A61M 16/12* (2006.01)
*A61M 16/10* (2006.01)

(52) U.S. Cl.
CPC ........ *A61M 16/18* (2013.01); *A61M 16/0003* (2014.02); *A61M 16/12* (2013.01); *A61M 2016/1035* (2013.01)

(58) Field of Classification Search
None
See application file for complete search history.

(56) References Cited

U.S. PATENT DOCUMENTS 4,881,541 A * 11/1989 Eger, II ................ A61M 16/18
128/203.14
5,546,931 A * 8/1996 Rusz .................... A61M 16/18
128/203.14
5,558,083 A   9/1996 Bathe et al.
(Continued)

FOREIGN PATENT DOCUMENTS

DE   102016001383 A1   8/2017
EP   0659445 A1   6/1995

OTHER PUBLICATIONS

Burte E P et al: "Mi crosystems for measurement and dosage of volatile anesthetics and respirative gases in anesthetic equipment", Micro Electro Mechanical Systems, 1998. MEMS 98. Proceedings., The Eleventh Annual International Workshop on Heidelberg, Germany Jan. 25-29, 1998, New York, NY, USA,IEEE, US, Jan. 25, 1998 (Jan. 25, 1998), pp. 510-514, XP010270162, DOI: 10.1109/MEMSYS.1998.659810 +.

*Primary Examiner* — Samchuan C Yao
*Assistant Examiner* — Tina Zhang
(74) *Attorney, Agent, or Firm* — McGlew and Tuttle, P.C.

(57) ABSTRACT

An anesthetic dispensing device (100) includes a measuring unit (150) for determining an anesthetic concentration in an area of an outlet (142) of the anesthetic dispensing device. The measuring unit is configured to measure a first parameter (154) of a gas concentration-dependent characteristic between a mixer unit (140) and a second parameter (155) of the gas concentration-dependent characteristic in a second gas branch (120) or in an area of a breathing gas feed (112) of the anesthetic dispensing device by at least one sensor element (152). The measuring unit is further configured to determine the anesthetic concentration between the mixer unit and the outlet and to output a corresponding concentration signal (160) as a function of calibration information assigned to the second parameter and of the first parameter.

19 Claims, 5 Drawing Sheets

(56) References Cited

U.S. PATENT DOCUMENTS

| | | | |
|---|---|---|---|
| 5,967,141 A | 10/1999 | Heinonen | |
| 2006/0097453 A1* | 5/2006 | Feldman | A63F 13/22 |
| | | | 273/304 |
| 2007/0051163 A1 | 3/2007 | Wohltjen | |
| 2011/0155131 A1* | 6/2011 | Bottom | A61M 16/202 |
| | | | 128/203.14 |
| 2017/0224947 A1* | 8/2017 | Manigel | A61M 16/12 |
| 2020/0341037 A1* | 10/2020 | Serret | G01R 31/327 |
| 2021/0220603 A1* | 7/2021 | Bartels | A61M 16/024 |

* cited by examiner

ANESTHETIC DISPENSING DEVICE WITH A MEASURING UNIT

CROSS REFERENCE TO RELATED APPLICATIONS

This application claims the benefit of priority under 35 U.S.C. § 119 of German Application 10 2020 000 268.4, filed Jan. 17, 2020, the entire contents of which are incorporated herein by reference.

TECHNICAL FIELD

The present invention pertains to an anesthetic dispensing device with a measuring unit for determining an anesthetic concentration in the area of an outlet of the anesthetic dispensing device. The present invention pertains, furthermore, to a process for determining an anesthetic concentration in the area of an outlet of the anesthetic dispensing device.

TECHNICAL BACKGROUND

The use of an anesthetic dispensing device for enriching a breathing gas provided with an anesthetic and for dispensing such an enriched gas mixture to an anesthesia breathing circuit connected to a patient is known. A first gas branch with an anesthetic evaporator is typically used here in order to enrich the breathing gas fed with the anesthetic. Furthermore, a second gas branch, also called bypass branch, is typically passed by the anesthetic evaporator in order to provide a diluted gas mixture enriched with the anesthetic within the framework of feeding both gas branches to a mixer unit.

For controlling the dispensing of the anesthetic, it is proposed in U.S. Pat. No. 5,967,141 that the anesthetic concentration be determined at an outlet of the anesthetic dispensing device and that the dispensing be changed by a control of the gas flow through the gas branches if the determined anesthetic concentration is not identical to a predefined desired concentration.

SUMMARY

An object of the present invention is to provide an especially simple determination of the anesthetic concentration, especially an especially robust determination of the anesthetic concentration in an area of an outlet of an anesthetic dispensing device.

An anesthetic dispensing device with a measuring unit for determining an anesthetic concentration in the area of an outlet of the anesthetic dispensing device, further having a first gas branch, a second gas branch, an anesthetic evaporator and a mixer unit is proposed according to the present invention to accomplish this object.

The first gas branch can be connected to a breathing gas feed and is configured to carry a breathing gas through the anesthetic evaporator to the mixer unit.

The second gas branch can be connected to the breathing gas feed and is configured to likewise carry the breathing gas to the mixer unit.

The anesthetic evaporator is arranged and configured to enrich the breathing gas in the first gas branch with an anesthetic.

The mixer unit is arranged and configured to mix the breathing gas, which is enriched with the anesthetic and is coming from the first gas branch, with the breathing gas from the second gas branch and to provide the gas mixture formed thereby to the outlet of the anesthetic dispensing device.

The measuring unit is configured to measure by means of a sensor element a first parameter of a gas concentration-dependent characteristic between the mixer unit and the outlet and to measure a second parameter of the gas concentration-dependent characteristic in the second gas branch or in the area of the breathing gas feed. The measuring unit is further configured to determine, especially to calculate, the anesthetic concentration between the mixer unit and the outlet depending on calibration information assigned to the second parameter, especially predefined calibration information, and at least the second parameter, and at least with the first parameter, especially a difference between the first parameter and the second parameter, and to output a corresponding concentration signal. The concentration signal indicates, in this case, the determined anesthetic concentration.

It was found within the framework of the present invention that a measurement of a gas concentration-dependent characteristic at two locations within the anesthetic dispensing device, namely, for the breathing gas not enriched with the anesthetic and for the enriched breathing gas in the area of the outlet, makes it possible to provide a measuring unit having a simple structure, especially a measuring unit with an unselective sensor element. Thus, the measuring unit according to the present invention is not preferably configured to determine an anesthetic concentration from an individual parameter of the gas concentration-dependent characteristic. The determination of the anesthetic concentration between the mixer unit and the outlet rather becomes preferably possible only by taking into account both parameters with the use of calibration information assigned to one parameter.

The provision of a sensor element that is unselective in this sense within the measuring unit makes it possible to use an especially robust measuring unit. Furthermore, an especially cost-effective determination of the anesthetic concentration is made possible hereby.

The determination of the anesthetic concentration directly in the area of the outlet of the anesthetic dispensing device makes it possible to precisely predict the anesthetic concentration that is fed to a patient during the use of the anesthetic dispensing device.

By providing an especially cost-effective determination of the anesthetic concentration, a cost-effective redundant measurement of the gas concentration-dependent characteristic and/or determination of the anesthetic concentration can advantageously be provided. This redundant measurement makes possible an automated mutual monitoring of components of the anesthetic dispensing device. As a result, it is possible, in particular, to reduce the risk of an undetected malfunction of the measuring unit or the risk of a late detection of a malfunction of the measuring unit.

Different prior-art volatile anesthetics, for example, isoflurane, sevoflurane and desflurane, may advantageously be used for the anesthetic dispensing device according to the present invention. This requires only that corresponding calibration information concerning the corresponding volatile anesthetic be taken into account according to the present invention.

The measurement between the mixer unit and the outlet also includes according to the present invention the measurement directly at the outlet or directly at the mixer unit.

The gas concentration-dependent characteristic may comprise, for example, a temperature of the gas within the framework of a thermal conductivity measurement, the density of the gas and/or a spectral property of the gas. The structure of the at least one sensor element of the measuring unit depends on which gas concentration-dependent characteristic is measured in the breathing gas.

The calibration information assigned to the second parameter is determined according to the present invention in order to detect thereby the influence of the anesthetic on the gas concentration-dependent characteristic. Thus, the selection of the calibration information does not depend according to the present invention on the anesthetic concentration, but only on the second parameter, i.e., the parameter measured in the second gas branch without anesthetic. Based on this calibration information, the anesthetic concentration is consequently determined according to the present invention depending on the first parameter, i.e., depending on a parameter measured in the gas containing anesthetic. The calibration information may also be used in this case on the basis of a difference between the first parameter and the second parameter or on the basis of another variable, which is obtained from the first parameter or from the first and second parameters.

The calibration information may also comprise a plurality of calibration information. In particular, the calibration information preferably makes it possible to determine the anesthetic used in the anesthetic evaporator on the basis of the first parameter or of a determined difference between the first parameter and the second parameter. The measurement of the second parameter preferably makes it possible to determine the composition of the fresh gas fed as breathing gas, e.g., the ratio of oxygen to laughing gas or of oxygen to nitrogen in the fed breathing gas, especially for the preferred case in which the components of the fed breathing gas are known, for example, they are known by a user input. The anesthetic concentration can be determined on the basis of such a known ratio by measuring the first parameter or the difference of the two parameters. Calibration information for the anesthetic that can be used in the anesthetic evaporator is preferably available for this purpose. The calibration information is available according to the present invention at least for one anesthetic. The plurality of calibration information preferably makes it possible to use the anesthetic dispensing device according to the present invention for different common breathing gases to be fed, e.g., an oxygen-nitrogen mixture and an oxygen-laughing gas mixture.

The calibration information is preferably predefined calibration information. The calibration information is predefined based on the fact that it is stored prior to an operation (inn an associated memory) or was generated at least prior to the current operation of the anesthetic dispensing device according to the present invention, for example, generated during an earlier operation of the device and stored in the associated memory.

The calibration information may be present according to the present invention, for example, in the form of a set of characteristic curves, of a functional dependence and/or of a value table. Different pieces of calibration information are available according to the present invention for different second parameters, so that the calibration information to be used is known after the measurement of the second parameter and this calibration information is used in combination with at least the first measured value, especially with a difference of the first and second measured values, in order to determine the anesthetic concentration.

The assignment of the calibration information to the second parameter is carried out, for example, by a characteristic curve, by a function or by other assignment rules.

Calibration information is defined within the framework of the present invention as the totality of all information used, especially all predefined information, via which the two measured parameters are analyzed. In addition to the calibration information assigned to the second parameter, the calibration information is consequently also used to provide the assignment between the second parameter and the assigned calibration information. Details of the corresponding analysis are explained within the framework of the description of the figures.

The concentration signal may be outputted, for example, to a user of the anesthetic dispensing device and/or to a control unit for controlling the enrichment of the breathing gas with anesthetic.

The at least one sensor element of the measuring unit according to the present invention must typically be arranged in contact with the breathing gas to be tested in order to measure the gas concentration-dependent characteristic.

The measuring unit according to the present invention may comprise a plurality of modules, for example, a plurality of modules comprising a sensor element each. The measuring unit may correspondingly have a one-part or multipart configuration.

The measuring unit preferably has a processor, which carries out the determination according to the present invention of the anesthetic concentration. The processor may be arranged in the immediate vicinity of the at least one sensor element or, as an alternative, at a spaced location from the sensor element, for example, in a separate module.

The configuration of an anesthetic evaporator and of a mixer unit are, in principle, known to the person skilled in the art, so that this will not be explained in detail below. An anesthetic evaporator is defined within the framework of this patent application as any device that adds an anesthetic in the gaseous form to a fed gas stream. Thus, an anesthetic evaporator in the sense of the present invention also covers a device that brings about the addition of an anesthetic via a heating element, as this happens, e.g., in a device typically called an anesthetic vaporizer.

Within the framework of the present invention, the determination of a value based on predefined information is a determination of the value by direct use of the predefined information and/or by the use of information that is available on the basis of the predefined information, for example, the calibration information. The determination on the basis of and/or depending on predefined information may also be carried out with the use of additional information during this determination.

Preferred embodiments of the anesthetic dispensing device according to the present invention will be described below.

In an especially preferred embodiment, the measuring unit is configured to determine the anesthetic concentration as a function of the calibration information assigned to the second parameter and of a difference between the first measured value and the second measured value. An error in the analysis of the two parameters can especially advantageously be reduced hereby.

In an especially preferred embodiment, the measuring unit further comprises at least one switch, which is configured to be able to switch the at least one sensor element between the measurement of the first parameter and the measurement of the second parameter. A single sensor element may advantageously be used in this embodiment in order to measure the first and second parameters with a time offset in relation to one another. In a variant of this embodiment, the switch is a switch that sets a gas flow of the breathing gas based on its switch position and it thereby controls whether the at least one sensor element is currently measuring the first parameter or the second parameter. In another, additional or alternative variant, the positioning of the corresponding sensor element is set via the position of the switch.

In an especially preferred embodiment of the anesthetic dispensing device according to the present invention, the at least one sensor element measures the gas concentration-dependent characteristic based on a thermal conductivity measurement. The thermal conductivity measurement is based in this case (as is typical) on a temperature measurement to determine the conductivity of a measured gas heated to a reference temperature. The corresponding gas concentration-dependent characteristic can be determined hereby in an especially simple manner and with a low susceptibility to error. In an alternative or additional embodiment, the at least one sensor element measures the parameters on the basis of an ultrasound measurement, of a density measurement and/or of an optical measurement of spectral properties of the breathing gas.

In another preferred embodiment, the measuring unit has at least two sensor elements, wherein a first sensor element of the at least two sensor elements is arranged and configured to measure at least the first parameter of the gas concentration-dependent characteristic between the measuring unit and the outlet, and wherein a second sensor element of the least two sensor elements is arranged and configured to measure at least the second parameter of the gas concentration-dependent characteristic in the second gas branch or in the area of the breathing gas feed. In this embodiment, the at least two sensor elements can measure simultaneously the first parameter and the second parameter of the gas concentration-dependent characteristic and thereby make possible an especially precise and rapid determination of the anesthetic concentration currently present in the area of the outlet. In particular, a fluctuation in the pressure and/or in the concentration during the measurement of the two parameters can be taken into account uniformly during a simultaneous or nearly simultaneous measurement. The at least two sensor elements may be arranged in a common housing or in modules of the measuring unit according to the present invention, which are separated in space.

In an especially advantageous variant of the preceding embodiment, the measuring unit comprises at least two switches, wherein the first sensor element of the at least two sensor elements is connected to a first switch of the at least two switches and wherein the second sensor element of the at least two sensor elements is connected to a second switch of the at least two switches. The first switch and the second switch are configured, in this case, to be able to switch between the measurement of the first parameter and the measurement of the second parameter by the respective connected sensor element. A malfunction of a sensor element can be detected in this variant especially rapidly by the redundant measurement of the two parameters, which is made possible. Especially small measurement errors can be detected rapidly by a comparison of the respective parameter determined via the first sensor element and via the second sensor element. In order to make a redundant measurement of the two parameters possible, the switch position of the two switches is changed preferably repeatedly in this variant. The switching of the switches may be triggered manually or automatically. A manual triggering of switching takes place, for example, via a user interface of the anesthetic dispensing device. An automated switching is carried out, for example, by a processor of the measuring unit or via a separate control unit of the anesthetic dispensing device. The switch position of the two switches is preferably changed at regular time intervals in an automated manner in order to rapidly detect a malfunction of a sensor element without manual support.

In an especially advantageous example of the preceding variant, the first switch and the second switch are coupled with one another, especially coupled mechanically, such that a change of a first switch position of the first switch also brings about a change of a second switch position of the second switch. Measurement of the same parameter simultaneously by both sensor elements is avoided in this example. Thus, it is ensured in this example that both parameters of the gas concentration-dependent characteristic are always determined simultaneously or essentially simultaneously.

In an especially preferred embodiment, the measurement of the first parameter and the measurement of the second parameter by the measuring unit take place essentially simultaneously. The current first parameter and the current second parameter can be determined hereby and the anesthetic concentration between the mixer unit and the outlet can consequently be determined especially precisely via the calibration information. In particular, errors based on pressure and/or concentration fluctuations can be avoided during this determination.

In another advantageous embodiment, the calibration information comprises a plurality of breathing gas composition-dependent calibration curves, especially at least a respective breathing gas composition-dependent calibration curve for an oxygen-nitrogen mixture and for an oxygen-laughing gas mixture. It is advantageously possible in this embodiment to select among a plurality of different breathing gases to be fed for the anesthetic dispensing device, without this requiring a separate calibration or adaptation of the device. The anesthetic dispensing device, especially the measuring unit of the anesthetic dispensing device, is preferably configured to determine the breathing gas used in an automated manner on the basis of the two measured parameters and the calibration information. An exemplary embodiment for such an analysis of the breathing gas used will be explained within the framework of the description of the figures. As an alternative or in addition, the calibration information comprises respective breathing gas composition-dependent calibration information for an oxygen-argon-laughing gas mixture and/or for an oxygen-xenon mixture.

In another embodiment, the measuring unit has a number of measured gas carrying ducts, in which the measurement of the first and second parameters is carried out. This number of measured gas carrying ducts is preferably integrated pneumatically into the breathing gas duct of the anesthetic dispensing device such that temporary pressure fluctuations within the first and/or second gas branches are also present at least partially in a corresponding manner within the number of first and/or second measured gas carrying ducts. It can be ensured hereby that temporary pressure fluctuations do not affect the accuracy of the measurement of the two parameters. The measured gas carrying ducts preferably have a smaller cross-sectional area than the two gas branches, because only a small measured gas volume is necessary for the measurement of the two parameters. Due to the smaller cross-sectional area, the carrying of the breathing gas to the outlet is affected only slightly or is not affected essentially by the measurement of the two parameters. The influence of the measurement on the breathing gas volume is preferably so minor due to the small cross-section area of a respective measured gas carrying duct that it does not compromise the breathing gas volume provided at the outlet in a manner perceptible for the user of the anesthetic dispensing device. Especially advantageous is the provision of the first and second sensor elements in a variant of this embodiment because the same breathing gas volume, which was removed from the breathing gas between the mixer unit and the outlet for measuring a parameter, is returned via a second measured gas carrying duct for the measurement of the other parameter within the framework of the simultaneous measurement of the two parameters. The influence of the measurement on the breathing gas volume provided at the outlet can be kept very small hereby.

In another embodiment, the anesthetic dispensing device according to the present invention further has a control unit, which is configured to receive the outputted concentration signal and to control the enrichment of the breathing gas with anesthetic in the first gas branch based on a comparison between a predefined desired anesthetic concentration and the determined anesthetic concentration. The predefined desired anesthetic concentration may be entered, for example, via a user interface of the anesthetic dispensing device. The enrichment of the breathing gas may be controlled, for example, via a control of the breathing gas volume within the first gas branch, via a control of the anesthetic volume within the anesthetic evaporator, via a control of the temperature within the anesthetic evaporator or via a control of the pressure within the anesthetic evaporator or the like. Such processes for controlling the anesthetic concentration are known and will not therefore be explained in detail below.

In a variant of the above embodiment, the control unit is further configured to determine a travel time correction signal based on the control of the breathing gas volume within the first gas branch and to output it to the measuring unit. The measuring unit is further configured to receive the travel time correction signal and to determine the anesthetic concentration based on the travel time correction signal. The travel time correction signal preferably shows a difference in the current travel time for the gas in the first and second gas branches. A difference in the composition of the breathing gas fed during the simultaneous measurement of the two parameters can advantageously be taken into account in this embodiment. For example, the parameters from the measuring unit are stored over a predefined time period and are corrected after the predefined time period in case of a change in composition, and the anesthetic concentration is determined and outputted to the control unit only after the predefined time period, preferably after at least 2 sec, especially after at least 5 sec, especially preferably after about 10 sec. In an alternative embodiment, not shown, the control unit is configured to offset the described travel time correction against the received concentration signal of the measuring unit, wherein the concentration signal preferably indicates a number of measured first and second parameters, which make it possible to offset the parameters against the travel time correction to determine the anesthetic concentration.

In an example of the preceding variant of the preceding embodiment, a measurement of a third parameter of the characteristic is provided for in the first gas branch in the flow direction of the breathing gas behind the anesthetic evaporator in order to improve the manner in which the travel time correction is taken into account. The third parameter indicates a change in the anesthetic concentration based on the travel time of the breathing gas being fed more rapidly than does the first parameter in the area of the outlet.

For example, a velocity of flow within the first gas branch can thus be inferred from the first and third parameters. Furthermore, a defect of the measuring unit or of an individual component of the measuring unit can be detected especially rapidly by the additional measurement, especially if an additional sensor is used.

The control unit is further configured in an especially preferred variant of the preceding embodiment to trigger a switching off of the anesthetic dispensing device if a difference between the determined anesthetic concentration and the predefined desired anesthetic concentration exceeds a predefined alarm threshold value. Such a switching off may be carried out, for example, by closing an additional alarm valve, which is arranged, for example, between the mixer and the outlet or in the first gas branch behind the anesthetic evaporator in the gas flow. It can be ensured by the switching off in this variant that an anesthetic concentration that is clearly too high is not fed into the anesthesia breathing circuit. The administration of an anesthetic concentration that is permanently too low can also be avoided by such an alarm mode and by the attention to incorrect operation, which was created thereby.

The concept according to the present invention of a measuring unit that measures the second parameter in the gas that is not yet mixed with anesthetic and measures the first parameter in the gas mixed with anesthetic and determines from this the anesthetic concentration based on the calibration information may, of course, also be carried out, in principle, in a single gas branch. In particular, this concept may also be applied to an anesthetic dispensing device that has only one gas branch with an anesthetic dispensing unit. This is possible, for example, if an anesthetic injection is used, during which the anesthetic concentration is regulated via a control of the injection volume rather than via a control of the gas flow. The concept of the measuring unit according to the present invention is, of course, likewise applicable to such a device structure. Any adaptations of the present invention to such a device that may be necessary are within the scope of the skill in the art.

According to another aspect of the present invention, a process for determining an anesthetic concentration in the area of an outlet of the anesthetic dispensing device is proposed to accomplish the above object. The process according to the present invention has the following steps:

provision of a first gas branch and of the second gas branch, wherein the first gas branch can be connected to a breathing gas feed and is configured to carry a breathing gas through an anesthetic evaporator to a mixer unit, and wherein the second gas branch can be connected to the breathing gas feed and is configured likewise to carry the breathing gas to the mixer unit, and wherein the mixer unit is arranged and configured to mix the breathing gas from the first gas branch, which breathing gas is enriched with an anesthetic with the breathing gas from the second gas branch and to provide the gas mixture formed thereby to an outlet of the anesthetic dispensing device;

measurement of a first parameter of a gas concentration-dependent characteristic between the mixer unit and the outlet;

measurement of a second parameter of the gas concentration-dependent characteristic in the second gas branch or in the area of the breathing gas feed;

determination of the anesthetic concentration between the mixer unit and the outlet based on calibration information assigned to the second parameter, especially on the basis of predefined calibration information and at least the first parameter; and outputting a concentration signal, which indicates the determined anesthetic concentration.

The process according to the present invention advantageously makes possible an especially robust determination of the anesthetic concentration because the anesthetic concentration is not determined via a single, complex measuring process, but the anesthetic concentration can be detected via two robust measurements of unselective parameters. It is possible as a result to use comparatively simple sensors, for example, temperature sensors, density sensors, ultrasound sensors and/or optical sensors for implementing the process according to the present invention.

In an especially preferred embodiment, the process according to the present invention further has the following steps:

receipt of the outputted concentration signal; and regulation of the enrichment of the breathing gas with anesthetic in the first gas branch based on a comparison between a predefined desired anesthetic concentration and the determined anesthetic concentration. The predefined desired anesthetic concentration is received, for example, via the user interface of the anesthetic dispensing device by a user input. As an alternative, the predefined desired anesthetic concentration is preset automatically, for example, in an automated manner depending on measured values of other medical devices, for example, an anesthesia device connected to the anesthetic dispensing device.

The present invention will be explained in more detail now based on advantageous exemplary embodiments shown schematically in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
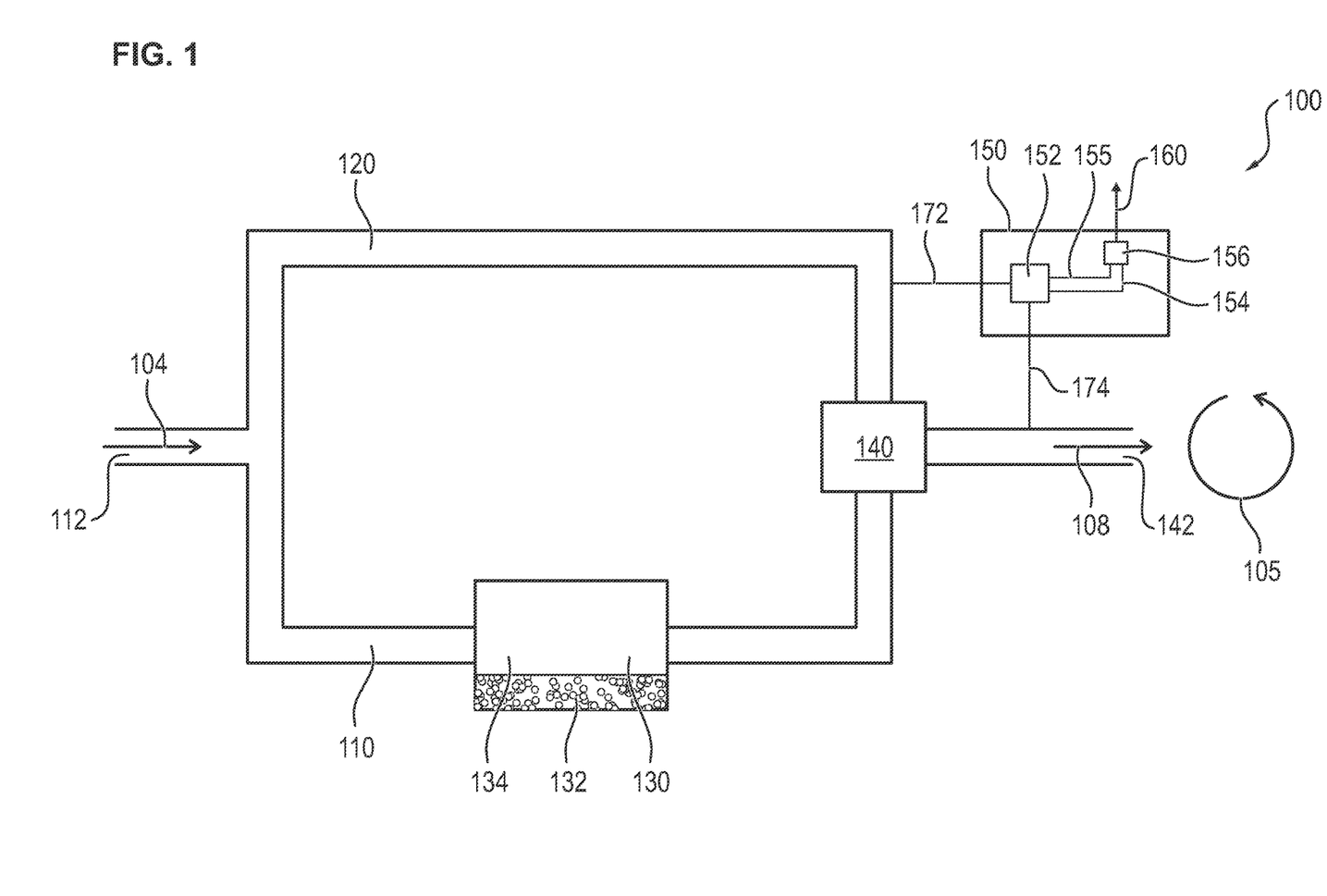
FIG. 1 is a schematic view of a first exemplary embodiment of an anesthetic dispensing device according to the present invention.

Referring to the drawings, FIG. 1 shows a schematic view of a first exemplary embodiment of an anesthetic dispensing device 100 according to the present invention.

The anesthetic dispensing device 100 comprises a first gas branch 110, a second gas branch 120, an anesthetic evaporator 130, a mixer unit 140 and a measuring unit 150.

The anesthetic dispensing device 100 is configured to set an anesthetic concentration in a gas mixture 108 to be provided to an anesthesia breathing circuit.

The first gas branch 110 can be connected to a breathing gas feed 112 and is configured to carry a breathing gas 104 through the anesthetic evaporator 130 to the mixer unit 140.

The second gas branch 120 can be connected to the breathing gas feed 112 and is configured likewise to carry the breathing gas 104 to the mixer unit 140. The two gas branches 110, 120 have a cavity each, through which the breathing gas 104 is carried and which is defined by a tubular wall.

The anesthetic evaporator 130 is arranged and configured to enrich the breathing gas 104 in the first gas branch 110 with an anesthetic 132. The anesthetic 132 is preferably located for this purpose in an evaporator chamber 134. The anesthetic 132 within the evaporator chamber 134 is typically in both the liquid form and in the gaseous form. The structure of such an evaporator chamber is generally known and will not therefore be explained in detail below.

The mixer unit 140 is arranged and configured to mix the breathing gas 104 from the first gas branch 110, which is enriched with the anesthetic 132, with the breathing gas 104 from the second gas branch 120 and to provide the gas mixture 108 formed thereby to an outlet 142 of the anesthetic dispensing device 100. The mixer unit 140 is arranged at a spaced location from the outlet 142 in the exemplary embodiment shown. In one exemplary embodiment, not shown, the mixer unit comprises the outlet of the anesthetic dispensing device.

The measuring unit 150 is configured to determine an anesthetic concentration in the area of the outlet 142 of the anesthetic dispensing device 100. It is configured to measure by at least one sensor element 152 a first parameter 154 of a gas concentration-dependent characteristic between the mixer unit 140 and the outlet 142 and to measure a second parameter 155 of the gas concentration-dependent characteristic in the second gas branch 120 or in the area of the breathing gas supply 112. In the exemplary embodiment shown, the first parameter 154 is measured in the flow direction directly in front of the outlet 142 and the second parameter 155 is measured in the second gas branch 120 in the area in front of the mixer unit 140. The gas concentration-dependent characteristic is the thermal conductivity of the gas mixture being tested. In one exemplary embodiment, not shown, the gas concentration-dependent characteristic is the density of the gas mixture being tested or an optical spectrum of the gas mixture being tested or the like. The measuring unit 150 in the exemplary embodiment being shown comprises exactly one sensor element 152. Measuring units that comprise exactly two sensor elements are shown within the framework of FIGS. 3 and 4 below. In exemplary embodiments that are not shown, the measuring unit according to the present invention comprises three or more sensor elements for measuring parameters of the gas concentration-dependent characteristic.

The measuring unit 150 is further configured according to the present invention to determine the anesthetic concentration between the mixer unit 140 and the outlet 142 as a function of calibration information assigned to the second parameter 155, especially predefined calibration information, and at least the first parameter 154 and to output a corresponding concentration signal 160.

In the exemplary embodiment shown, the gas concentration-dependent characteristic is determined within the framework of the first parameter 154 for a gas mixture, which comprises both the breathing gas fed via the breathing gas feed 112 and the breathing gas fed via the anesthetic evaporator 130. Within the framework of the second parameter 155, the gas concentration-dependent characteristic is determined for a gas mixture that comprises only the breathing gas fed to the gas mixture via the breathing gas feed 112 in the second gas branch 120. By determining the two parameters 154, 155, the influence of the anesthetic on the measured thermal conductivity can be determined. As is common in the area of thermal conductivity measurement, the gas is heated for the measurement of the thermal conductivity to a measurement temperature that exceeds the ambient temperature, for example, higher than 45° C., especially to about 50° C. An inaccuracy based on a temperature fluctuation is avoided hereby. Based on the second parameter 155, the breathing gas fed is inferred via the calibration information; in particular, it is inferred whether an oxygen-nitrogen mixture or an oxygen-laughing gas mixture was used. The calibration information comprises in the exemplary embodiment shown a plurality of breathing gas composition-dependent calibration curves, namely, a respective breathing gas composition-dependent calibration curve for an oxygen-nitrogen mixture and for an oxygen-laughing gas mixture. Based on the determined first parameter, the anesthetic concentration is then determined. In one exemplary embodiment, not shown, the anesthetic used is obtained from the second parameter via the composition of the breathing gas fed, which is known from the second parameter. The calibration information is preferably likewise used for this purpose.

The calibration information indicates in this case, for example, the dependence between the thermal conductivity in the second gas branch or in the area of the breathing gas feed and the ratio of the composition of the known, for example, predefined components of the fed breathing gas. This ratio can thus be determined by measuring the second parameter by means of the measuring unit. Furthermore, the calibration information preferably indicates for the determined ratio of the composition of the fed breathing gas the dependence between thermal conductivity in the area between the mixer unit and the outlet and the anesthetic concentration for the known, for example, predefined anesthetic. The anesthetic concentration can thus be determined by the first parameter on the basis of the calibration information assigned to the second parameter.

The calibration information used is determined, for example, by storing as a calibration curve a linear increase and a non-linear increase in thermal conduction as a function of the addition of an additional gas.

The calibration information preferably comprises a first characteristic curve, by which the composition of the fed gas is determined as a function of the second parameter. A second calibration curve, which describes a dependence between the first parameter or difference of the first and second parameters and the anesthetic concentration, can be assigned to this information. The second calibration curve is preferably selected as a function of the second parameter from the group of second calibration curves.

The calibration information may be present in the form of one or more data tables and/or in the form of one or more diagrams or characteristics or functions. Characteristic curves are also defined according to the present invention as curves. In the exemplary embodiment shown, the measuring unit 150 comprises a memory module (not shown), in which the calibration information is stored in the form of characteristic curves. Furthermore, the measuring unit 150 comprises in the exemplary embodiment shown a processor 156, which determines the anesthetic concentration in the manner according to the present invention as a function of the calibration information and the two parameters and outputs the corresponding concentration signal.

In one exemplary embodiment, not shown, the anesthetic concentration is determined on the basis of a density measurement by determining the density of the gas passed by the respective sensor. The calibration information and the process for determining the anesthetic concentration from the density measurement may be provided and carried out, for example, analogously to the procedure described in the preceding paragraphs concerning the measurement of the thermal conductivity. The second parameter is preferably also determined according to the present invention by a density measurement via a corresponding characteristic curve and the assigned calibration information is used on the basis of the second parameter in order to determine from it the anesthetic concentration at least on the basis of the first parameter.

The outputted concentration signal shows to a user of the anesthetic dispensing device 100 whether the desired anesthetic concentration is provided to the anesthesia breathing circuit 105. The concentration signal 160 indicates thereby, for example, a change to be performed manually in the anesthetic concentration over the anesthetic evaporator 130 if a desired anesthetic concentration was not yet reached by the anesthetic dispensing device 100.

In one exemplary embodiment, not shown, the processor of the measuring unit is arranged separated in space from the at least one sensor element. Furthermore, the measuring unit according to the present invention may comprise a plurality of modules separated in space or, for example, a single housing or a single enclosure of an anesthesia device.

The connection between the respective gas branch and the measuring unit 150 is brought about via a respective measured gas carrying duct 172, 174 in the exemplary embodiment shown. The measurement of the two parameters 154, 155 is carried out in the respective measured gas carrying duct 172, 174. The measurement of the second parameter 155 is carried out in this case via the first measured gas carrying duct 172 and the measurement of the first parameter 154 is carried out via the second measured gas carrying duct 174. The measured gas carrying ducts 172, 174 are integrated pneumatically into the breathing gas duct of the anesthetic dispensing device 100 such that temporary fluctuations within the first and/or second gas branches are also present at least partially in a corresponding manner within the two measured gas carrying ducts 172, 174. Such temporary pressure fluctuations will also be present within the two measured gas carrying ducts 172, 174, but in a possibly reduced manner based on the pneumatic structure. The respective measured gas carrying duct 172, 174 has a smaller cross section than the respective gas branch, preferably at most one fourth of the cross section of the gas branch, especially at most one tenth of the cross section of the gas branch, and especially preferably at most one 20th of the cross section of the gas branch. The area between the mixer unit 140 and the outlet 142 is also called a gas branch of the anesthetic dispensing device 100 in this case.

In one exemplary embodiment, not shown, the second parameter is measured in the area of the breathing gas feed. Like in the area of the second gas branch, the breathing gas is not enriched with an anesthetic in the area of the breathing gas feed, so that the procedure that can be followed in this exemplary embodiment, which is not shown, is analogous to the procedure described in the case of the determination of the anesthetic concentration.

The short length of the two measured gas carrying ducts 172, 174, which is made possible by the measurement of the second parameter in the area of the second gas branch 120, is especially advantageous in connection with the measurement of the second parameter in the area of the second gas branch 120, along with the advantage of the small buffer volume of the measured gas removed from the corresponding gas branch, which small buffer volume is associated therewith. For example, pressure fluctuations or fluctuations in the anesthetic concentration can be detected hereby especially rapidly by the measuring unit 150.

Figure 2:
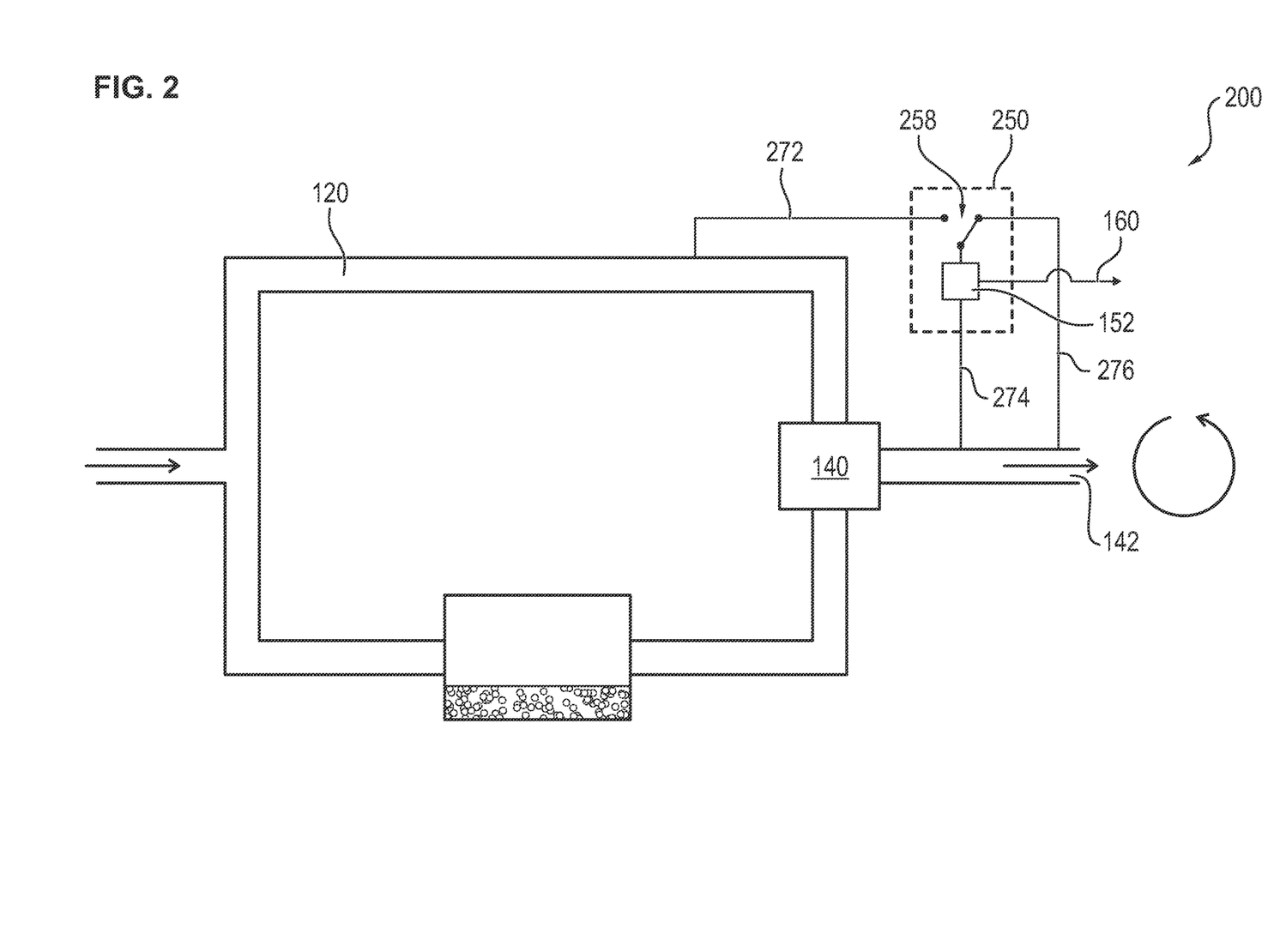
FIG. 2 is a schematic view of a second exemplary embodiment of the anesthetic dispensing device according to the present invention.

A possible structure of the measuring unit, which illustrates how the two parameters 154, 155 can be measured by a single sensor element 152, is shown within the framework of FIG. 2.

The different parts of the anesthetic dispensing device 100 according to the present invention are arranged in the exemplary embodiment shown in a common housing (not shown), which can be connected to the anesthesia breathing circuit 105. In another exemplary embodiment, the anesthetic dispensing device according to the present invention is integrated into an anesthesia device with a corresponding anesthesia breathing circuit. In another exemplary embodiment, the different parts of the anesthetic dispensing device according to the present invention are arranged at least partially in different housings.

Other components of a typical anesthetic dispensing device, for example, a valve, a seal, a gas flow-measuring device or the like, may likewise be parts of the anesthetic dispensing device according to the present invention, as appears directly from the present description of the teachings according to the present invention for a person skilled in the art.

FIG. 2 shows a schematic view of a second exemplary embodiment of the anesthetic dispensing device 200 according to the present invention.

The anesthetic dispensing device 200 shown differs from the anesthetic dispensing device 100 shown in FIG. 1 mainly in that the measuring unit 250 has a switch 258, with which it is possible to switch between the measurement of the first parameter and the measurement of the second parameter by the one sensor element 152.

The switching of the switch 258 takes place preferably at regular time intervals, the regular time intervals preferably being shorter than 60 sec, especially shorter than 40 sec, and especially preferably shorter than 20 sec. As a result, the measurement of the two parameters can be carried out with an only short offset in time. A short offset in time between the two measurements makes possible an especially accurate determination of the anesthetic concentration by the measuring unit 250, because pressure and/or concentration fluctuations can be taken into account uniformly during both measurements.

The measured gas carrying ducts 272, 274, 276 shown cause the respective gas mixture to be measured to flow through or arrive at the sensor element 152 in different directions at the sensor element 152 for both measurements. Thus, the gas stream to be measured is sent through the first measured gas carrying duct 272 to the sensor element 152 and then via the second measured gas carrying duct 274 to the outlet 142. By contrast, the gas stream to be measured is removed between the mixer unit 140 and the outlet 142 through the second measured gas carrying duct, is carried through the sensor element 152 and then carried via the switch 258 and the third measured gas carrying duct 276 back to the outlet 142 during the measurement of the first parameter.

The processing of the two parameters is not shown in the exemplary embodiment shown. This processing leads to the outputted concentration signal 160.

The switch 258 is an electrically operated toggle switch. This toggle switch is controlled via the measuring unit 250. The measuring unit 250 can infer as a result directly via the switch position of the switch 258 the currently measured parameter or the parameter to be currently measured and process the measurement result correspondingly. In one exemplary embodiment, not shown, the switch is a switch to be actuated manually. In addition to the toggle switch, a plurality of other switches are known to the person skilled in this field for such pneumatic applications and they will not therefore be explained in detail below. In another exemplary embodiment, not shown, switching between the measurement of the first parameter and the measurement of the second parameter is brought about by a change in the position in space of the at least one sensor element. As a result, switching between the two measurements is possible without any change having to be made in the carrying of the gas to be measured.

The switch 258 is preferably configured such that the measured gas carrying duct that is not used for the measurement of a parameter any longer is sealed off during a switching process such that no gas can escape in the area of the switch 258. It is ensured hereby that no more gas is removed in the corresponding gas branch of the anesthetic dispensing device 200 for the measurement of the parameter to be currently measured.

Figure 3:
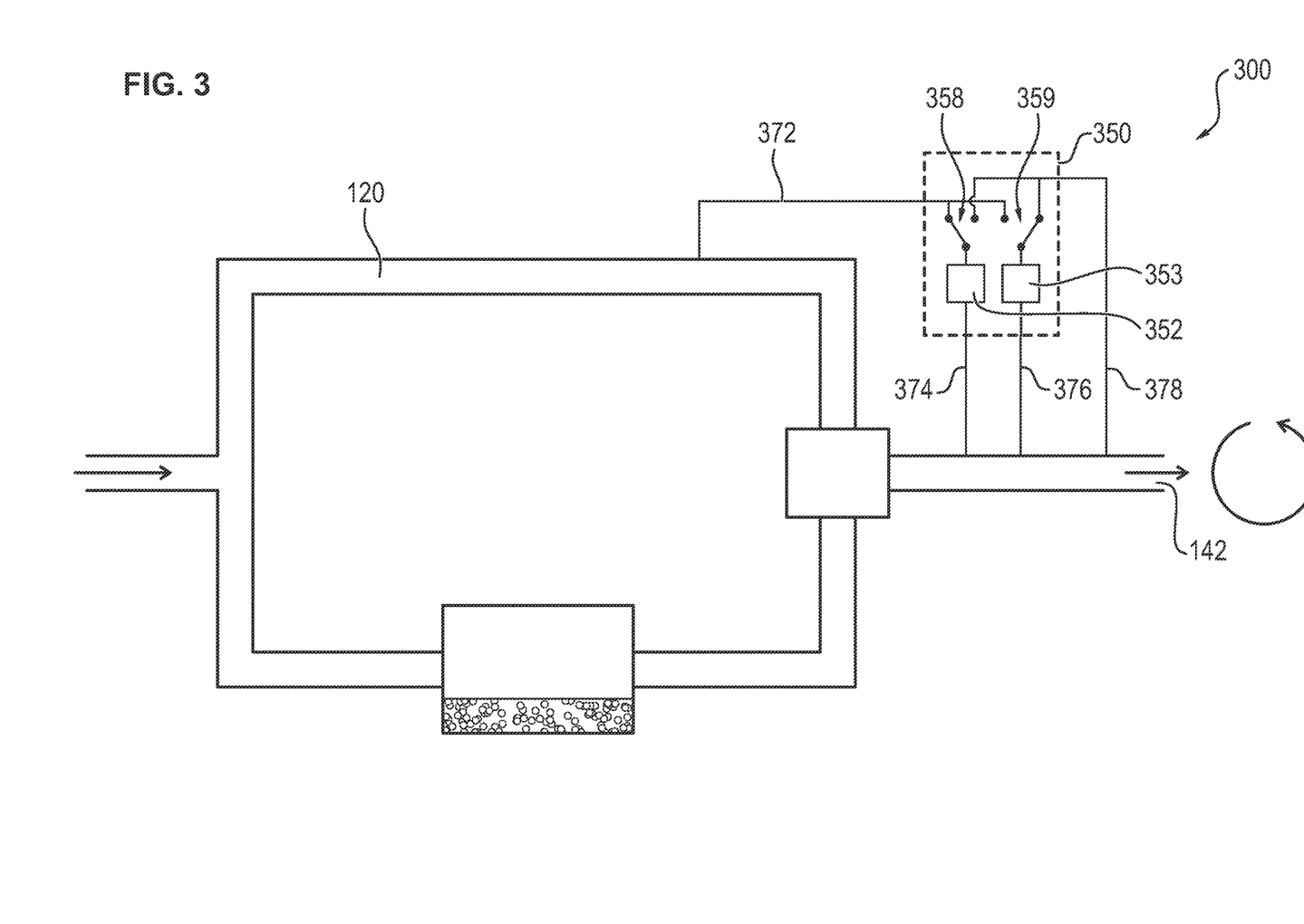
FIG. 3 is a schematic view of a third exemplary embodiment of the anesthetic dispensing device according to the present invention.

FIG. 3 shows a schematic view of a third exemplary embodiment of the anesthetic dispensing device 300 according to the present invention.

The anesthetic dispensing device 300 differs from the anesthetic dispensing device 200 shown in FIG. 2 in that the measuring unit 350 has two sensor elements 352, 353.

A respective switch 358, 359, via which the parameter of the two parameters to be measured by the sensor element 352, 353 assigned to the respective switch 358, 359 is set, is assigned to each of the two sensor elements 352, 353. Due to the circuitry shown, both sensor elements 352, 353 can measure both parameters depending on the current switch position of the respective switch 358, 359.

The first sensor element 352 is assigned to the first switch 358 and the second sensor element 353 is assigned to the second switch 359. The respective measured gas carrying ducts are arranged such that the two sensor elements 352, 353 can determine the same parameter simultaneously. Such a redundant measurement may be advantageous, for example, for checking the operability of both sensor elements.

A simultaneous measurement of the first and second parameters is possible in the switch position shown of the two switches 358, 359. The gas needed for the measurement is thus carried via the first measured gas carrying duct 372 from the second gas branch 120 to the first switch 358 and as a result to the first sensor element 352. It is carried from the first sensor element via the second measured gas carrying duct 374 into the area of the outlet 142 of the anesthetic dispensing device 300. For the measurement of the first parameter, the gas to be measured is carried from the area of the outlet 142 via the third measured gas carrying duct 376 to the second sensor element 353 and it is carried via the second switch 359 and a fourth measured gas carrying duct 378 to the outlet 142.

The two switches 358, 359 are controlled by the measuring unit 350 and can change their respective switch positions in the process independently from one another.

The output of the corresponding concentration signal is not shown in FIG. 3 for reasons of clarity.

Figure 4:
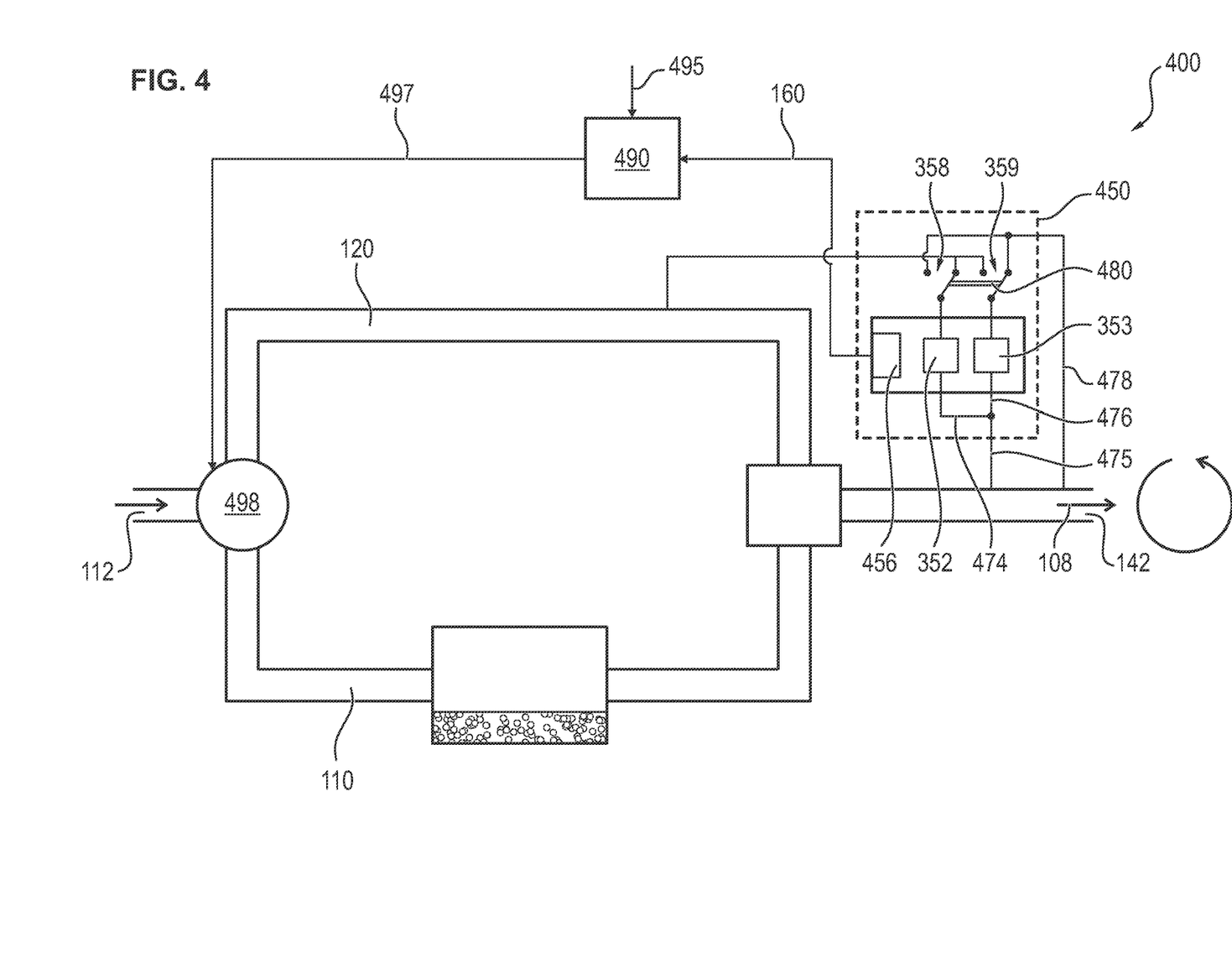
FIG. 4 is a schematic view of a fourth exemplary embodiment of the anesthetic dispensing device according to the present invention.

FIG. 4 shows a schematic view of a fourth exemplary embodiment of the anesthetic dispensing device 400 according to the present invention.

The anesthetic dispensing device 400 differs from the anesthetic dispensing device 300 shown in FIG. 3 in that the two switches 358, 359 are coupled with one another via a coupling element 480, especially mechanical coupling element 480. It is ensured by means of this coupling element 480 that a change of a first switch position of the first switch 358 also brings about a change of the second switch position of the second switch 359. As a result, the two sensor elements 352, 353 do not measure the same parameter simultaneously, but they always change between a state in which the first sensor element 352 measures the first parameter and the second sensor element 353 measures the second parameter, and a state in which the first sensor element 352 measures the second parameter and the second sensor element 353 measures the first parameter.

The simultaneous measurement of the two parameters makes possible an especially precise determination of the anesthetic concentration in the area of the outlet 142 of the anesthetic dispensing device 400. Furthermore, the change of the sensor element measuring just one parameter leads to a redundant measurement of both parameters and, as a result, to an operation of the device that can be checked reliably, because an error of a sensor element can be detected especially rapidly.

Furthermore, the anesthetic dispensing device 400 differs from the previously described exemplary embodiments in that it has, furthermore, a control unit 490, which receives the concentration signal 160 determined and outputted by the processor 456 of the measuring unit 450. Furthermore, the control unit 490, which has an associated memory, is configured to receive an input signal 495, which indicates a predefined desired anesthetic concentration. The input signal 495 may be provided, for example, by a user input at a user interface or by a central processing unit of an anesthesia device connected to the anesthetic dispensing device 400. Further, the control unit 490 is configured to send a control signal 497 to a flow control unit 498 on the basis of a comparison between the predefined desired anesthetic concentration and the determined anesthetic concentration indicated by the concentration signal 160. The flow control unit 498 is configured to distribute the gas flow from the breathing gas feed 112 into the first and second gas branches 110, 120. The control unit 490 is configured via the control signal 497 to actuate the flow control unit 498 such that the enrichment of the breathing gas with anesthetic in the first gas branch 110 is controlled on the basis of the comparison of the predefined desired anesthetic concentration and the determined anesthetic concentration. For example, a gas flow through the first gas branch 110 can be increased and the percentage of the breathing gas enriched with anesthetic in the gas mixture 108 at the outlet 142 can be increased thereby at a determined anesthetic concentration, which is below the desired anesthetic concentration.

In one exemplary embodiment, not shown, the control unit is configured, furthermore, to output, based on the controlled splitting of the gas flows through the first and second gas branches, a travel time correction signal to the measuring unit, which signal indicates a difference in the current travel time for gas in the first and second gas branches. Furthermore, the measuring unit is configured to determine the anesthetic concentration based on the travel time correction signal. A difference in the composition of the fed breathing gas during the simultaneous measurement of the two parameters can thus advantageously be taken into account. For example, the parameters of the measuring unit may be stored over a predefined time period and corrected in case of a change in the composition after the predefined time period, and the anesthetic concentration is determined and is outputted to the control unit only after the predefined time period, preferably after at least 2 sec, especially at least 5 sec, and especially preferably about 10 sec. In an alternative exemplary embodiment, not shown, the control unit is configured to offset the described travel time correction with the received concentration signal of the measuring unit, wherein the concentration signal preferably indicates a number of measured first and second parameters, which make it possible to offset the parameters with the travel time correction to determine the anesthetic concentration.

Finally, the anesthetic dispensing device 400 differs from the anesthetic dispensing device 300 in that the second and third measured gas carrying ducts 474, 476 have a common port 475 to the gas duct in the area of the outlet 142. This is made possible by the first parameter being determined by the corresponding measured gas being carried via the fourth measured gas carrying duct 478 to the second sensor element 353, so that, unlike in the anesthetic dispensing device 300, a measured gas flows through the second and third measured gas carrying ducts 474, 476 in the same direction.

Figure 5:
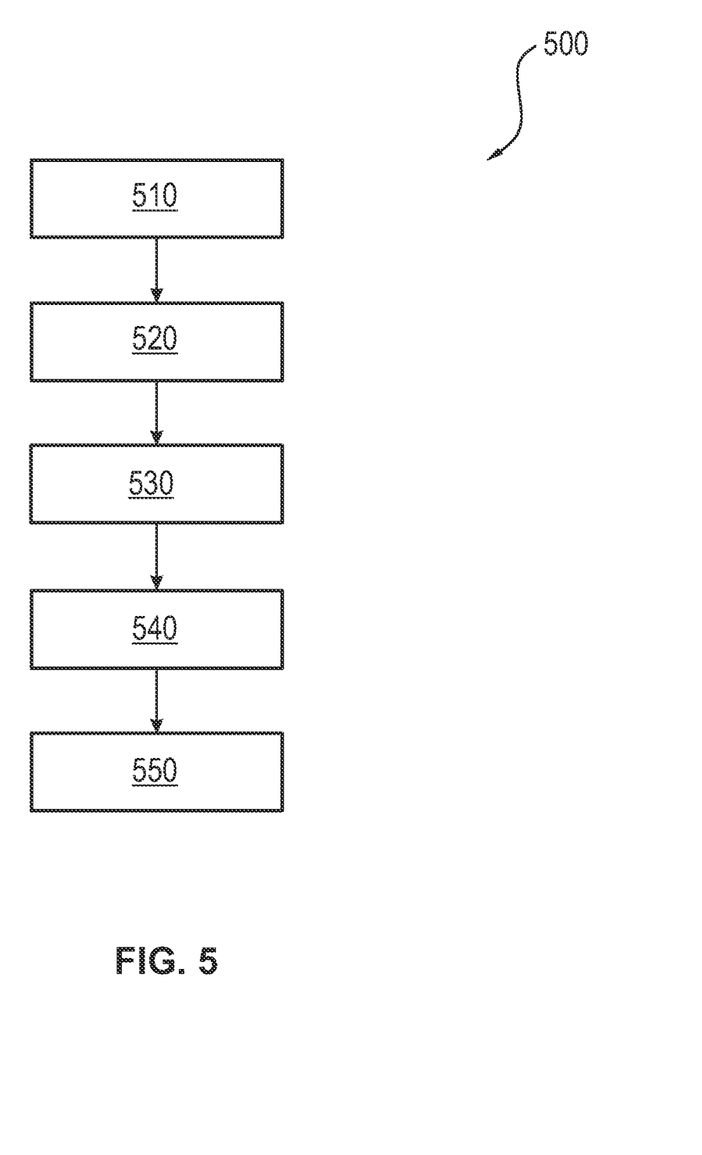
FIG. 5 is a flow chart of a first exemplary embodiment of a process according to another aspect of the present invention.

FIG. 5 shows a flow chart of a first exemplary embodiment of a process 500 according to another aspect of the present invention.

The process 500 is configured to determine an anesthetic concentration in the area of an outlet of an anesthetic dispensing device. It has the steps 510 through 550 described below.

A first step 510 comprises the provision of a first and second gas branches, wherein the first gas branch can be connected to a breathing gas feed and is configured to carry a breathing gas through an anesthetic evaporator to a mixer unit, and wherein the second gas branch can be connected to the breathing gas feed and is configured to likewise carry the breathing gas to the mixer unit. The mixer unit is arranged and configured in this case to mix the breathing gas from the first gas branch, which breathing gas is enriched with an anesthetic, with the breathing gas from the second gas branch and to provide the gas mixture formed thereby to an outlet of the anesthetic dispensing device.

A next step 520 comprises a measurement of a first parameter of a gas concentration-dependent characteristic between the mixer unit and the outlet.

A next step 530 comprises a measurement of a second parameter of the gas concentration-dependent characteristic in the second gas branch or in the area of the breathing gas feed.

An additional step 540 comprises a determination of the anesthetic concentration between the mixer unit and the outlet on the basis of calibration information assigned to the second parameter and at least of the first parameter.

A final step 550 comprises the outputting of a concentration signal, which indicates the determined anesthetic concentration.

Step 510 is preferably carried out during the manufacture of the anesthetic dispensing device according to the present invention and it is not repeated thereafter. Steps 520 and 530 may be carried out in different orders and they are, in principle, independent from one another. However, there should be a short time interval between the carrying out of steps 520 and 530 for determining the anesthetic concentration as accurately as possible. Steps 540 and 550 are carried out in this order, after the two parameters have been measured within the framework of steps 520 and 530.

The measurement within the framework of steps 520 and 530 is preferably carried out at regular time intervals. The regular time intervals preferably comprise time intervals that are shorter than 60 sec, especially shorter than 40 sec, and especially preferably shorter than 20 sec. As an alternative or in addition, the measurement of the two parameters and hence steps 520 and 530 may be carried out again after the outputting of the concentration signal within the framework of step 550.

In an especially preferred variant of this embodiment, the process further comprises the following steps, which are preferably carried out after step 550:

receipt of the outputted concentration signal; and regulation of the enrichment of the breathing gas with anesthetic in the first gas branch on the basis of a comparison between a predefined desired anesthetic concentration and the determined anesthetic concentration.

The determined anesthetic concentration can be used in this variant directly in order to ensure that the enrichment of the breathing gas with the anesthetic takes place such that the predefined desired anesthetic concentration is reached.

The predefined desired anesthetic concentration may be preset, for example, via a user input at a corresponding user interface of the anesthetic dispensing device.

While specific embodiments of the invention have been shown and described in detail to illustrate the application of the principles of the invention, it will be understood that the invention may be embodied otherwise without departing from such principles.

LIST OF REFERENCE NUMBERS

100, 200, 300, 400 Anesthetic dispensing device
104 Breathing gas
105 Anesthesia breathing circuit
108 Gas mixture
110 First gas branch
112 Breathing gas feed
120 Second gas branch
130 Anesthetic evaporator
132 Anesthetic
134 Evaporator chamber
140 Mixer unit
142 Outlet
150, 250, 350, 450 Measuring unit
152 Sensor element
154 First parameter
155 Second parameter
156, 456 Processor
160 Concentration signal
172, 272, 372 First measured gas carrying duct
174, 274, 374, 474 Second measured gas carrying duct
258, 358 First switch
276, 376, 476 Third measured gas carrying duct
352 First sensor element
353 Second sensor element
359 Second switch
378, 478 Fourth measured gas carrying duct
475 Common port
480 Coupling element
490 Control unit
495 Input signal
497 Control signal
498 Flow control unit
500 Process
510, 520, 530, 540, 550 Steps of the process

What is claimed is:

1. An anesthetic dispensing device comprising:

an anesthetic evaporator;

a mixer unit;

a first gas branch configured to be connected to a breathing gas feed and configured to carry a breathing gas through the anesthetic evaporator to the mixer unit;

a second gas branch configured to be connected to the breathing gas feed and configured to carry the breathing gas to the mixer unit, wherein the anesthetic evaporator is arranged and configured to enrich the breathing gas in the first gas branch with an anesthetic and the mixer unit is arranged and configured to mix the breathing gas from the first gas branch, which breathing gas is enriched with the anesthetic, with the breathing gas from the second gas branch and to provide the gas mixture formed thereby to an outlet of the anesthetic dispensing device; and a measuring unit for determining an anesthetic concentration in an area of the outlet of the anesthetic dispensing device, the measuring unit comprising at least one sensor element, the measuring unit further comprising a first sensor element, a second sensor element and at least two switches, the first sensor element being connected to a first switch of the at least two switches, the second sensor element being connected to a second switch of the at least two switches, wherein the measuring unit is configured:

to measure a first parameter of a gas concentration-dependent characteristic between the mixer unit and the outlet;

to measure a second parameter of the gas concentration-dependent characteristic in the second gas branch or in the area of the breathing gas feed, the first sensor element being configured to measure at least one of the first parameter and the second parameter, the second sensor element being configured to measure one or more of the first parameter and the second parameter, the first and second switches being configured to be switched between the measurement of the first parameter and the measurement of the second parameter by the respective connected sensor element; and to determine the anesthetic concentration between the mixer unit and the outlet as a function of calibration information assigned to the second parameter and at least as a function of the first parameter and to output a corresponding concentration signal.

2. An anesthetic dispensing device in accordance with claim 1, wherein the measuring unit is configured to determine the anesthetic concentration as a function of the calibration information assigned to the second parameter and a difference between a first measured value and a second measured value.

3. An anesthetic dispensing device in accordance with claim 1, wherein each of the first sensor element and the second sensor element are configured to measure the first parameter of the gas concentration-dependent characteristic and the second parameter of the gas concentration-dependent characteristic based on a thermal conductivity measurement or of a density measurement.

4. An anesthetic dispensing device in accordance with claim 1, wherein the first switch and the second switch are coupled with one another such that a change of a first switch position of the first switch also brings about a change of a second switch position of the second switch.

5. An anesthetic dispensing device in accordance with claim 1, wherein the measurement of the first parameter and the measurement of the second parameter are carried out by the measuring unit essentially simultaneously.

6. An anesthetic dispensing device in accordance with claim 1, wherein the calibration information comprises a plurality of breathing gas composition-dependent calibration curves.

7. An anesthetic dispensing device in accordance with claim 6, wherein the plurality of breathing gas composition-dependent calibration curves comprise at least a breathing gas composition-dependent calibration curve for an oxygen-nitrogen mixture and a breathing gas composition-dependent calibration curve for an oxygen-laughing gas mixture.

8. An anesthetic dispensing device in accordance with claim 1, wherein the measuring unit comprises a number of measured gas carrying ducts, in which the measurement of the first and second parameters is carried out and which are pneumatically integrated into the breathing gas duct of the anesthetic dispensing device such that temporary pressure fluctuations within the first and/or second gas branch are also present at least partly in a corresponding manner within the number of measured gas carrying ducts.

9. An anesthetic dispensing device in accordance with claim 1, further comprising a control unit configured to receive the outputted concentration signal and to control the enrichment of the breathing gas with anesthetic in the first gas branch on the basis of a comparison between a predefined desired anesthetic concentration and the determined anesthetic concentration.

10. A process for determining an anesthetic concentration in an area of an outlet of an anesthetic dispensing device, the process comprising the steps of:
providing a first gas branch and a second gas branch, wherein the first gas branch is configured to be connected to a breathing gas feed and is configured to carry a breathing gas through an anesthetic evaporator to a mixer unit, and wherein the second gas branch s configured to be connected to the breathing gas feed and is configured to carry the breathing gas to the mixer unit, and wherein the mixer unit is arranged and configured to mix the breathing gas from the first gas branch, which breathing gas is enriched with an anesthetic, with the breathing gas from the second gas branch and to provide the gas mixture formed thereby for an outlet of the anesthetic dispensing device, the measuring unit further comprising a first sensor element, a second sensor element and at least two switches, the first sensor element being connected to a first switch of the at least two switches, the second sensor element being connected to a second switch of the at least two switches,
measuring a first parameter of a gas concentration-dependent characteristic between the mixer unit and the outlet;
measuring a second parameter of the gas concentration-dependent characteristic in the second gas branch or in an area of the breathing gas feed, the first sensor element being configured to measure at least one of the first parameter and the second parameter, the second sensor element being configured to measure one or more of the first parameter and the second parameter, the first and second switches being configured to be switched between the measurement of the first parameter and the measurement of the second parameter by the respective connected sensor element;
determining an anesthetic concentration between the mixer unit and the outlet based on calibration information assigned to the second parameter and at least the first parameter; and
outputting a concentration signal, which indicates the determined anesthetic concentration.

11. A process in accordance with claim 10, further comprising the steps of:
receiving the outputted concentration signal; and
regulating the enrichment of the breathing gas with anesthetic in the first gas branch on the basis of a comparison between a predefined desired anesthetic concentration and the determined anesthetic concentration.

12. A process in accordance with claim 10, wherein the first switch comprises a first switch first position and a first switch second position, the first sensor element being configured to measure the first parameter with the first switch in the first switch first position, the first sensor element being configured to measure the second parameter with the first switch in the first switch second position.

13. A process in accordance with claim 10, wherein the second switch comprises a second switch first position and a second switch second position, the second sensor element being configured to measure the first parameter with the second switch in the second switch first position, the second sensor element being configured to measure the second parameter with the second switch in the second switch second position.

14. A process in accordance with claim 10, wherein the first switch comprises a first switch first position and a first switch second position, the first sensor element being configured to measure the first parameter with the first switch in the first switch first position, the first sensor element being configured to measure the second parameter with the first switch in the first switch second position, the second switch comprising a second switch first position and a second switch second position, the second sensor element being configured to measure the first parameter with the second switch in the second switch first position, the second sensor element being configured to measure the second parameter with the second switch in the second switch second position.

15. A process in accordance with claim 10, wherein the first sensor element and the second sensor element are configured to simultaneously measure at least one of the first parameter and the second parameter.

16. An anesthetic dispensing device in accordance with claim 1, wherein the first switch comprises a first switch first position and a first switch second position, the first sensor element being configured to measure the first parameter with the first switch in the first switch first position, the first sensor element being configured to measure the second parameter with the first switch in the first switch second position.

17. An anesthetic dispensing device in accordance with claim 1, wherein the second switch comprises a second switch first position and a second switch second position, the second sensor element being configured to measure the first parameter with the second switch in the second switch first position, the second sensor element being configured to measure the second parameter with the second switch in the second switch second position.

18. An anesthetic dispensing device in accordance with claim 1, wherein the first switch comprises a first switch first position and a first switch second position, the first sensor element being configured to measure the first parameter with the first switch in the first switch first position, the first sensor element being configured to measure the second parameter with the first switch in the first switch second position, the second switch element comprising a second switch first position and a second switch second position, the second sensor element being configured to measure the first parameter with the second switch in the second switch first position, the second sensor element being configured to measure the second parameter with the second switch in the second switch second position.

19. An anesthetic dispensing device in accordance with claim 1, wherein the first sensor element and the second sensor element are configured to simultaneously measure at least one of the first parameter and the second parameter.

* * * * *